United States Patent [19]

Kabbe et al.

[11] 4,328,223

[45] May 4, 1982

[54] 2-AMINO-3A,4,5,6-TETRAHYDRO-PERIMIDINE DERIVATIVES AND THEIR MEDICINAL USE IN COMBATTING CIRCULATORY DISEASES

[75] Inventors: Hans-Joachim Kabbe; Hildegard E. Mayer; Annedore Mayer; Andrea Mayer; Heinz Ziemann, all of Leverkusen; Kurt Stoepel, Wuppertal-Elberfeld, all of Fed. Rep. of Germany

[73] Assignee: Bayer Aktiengesellschaft, Leverkusen, Fed. Rep. of Germany

[21] Appl. No.: 27,538

[22] Filed: Apr. 5, 1979

[30] Foreign Application Priority Data

Apr. 14, 1978 [DE] Fed. Rep. of Germany ....... 2816123
Sep. 8, 1978 [DE] Fed. Rep. of Germany ....... 2839137

[51] Int. Cl.$^3$ .................... A61K 31/506; A61K 31/54; C07D 239/70; C07D 403/04
[52] U.S. Cl. ................................. 424/246; 424/248.4; 424/251; 544/60; 544/115; 544/249
[58] Field of Search .......................... 544/249, 115, 60; 424/251, 246, 248.4

[56] References Cited

U.S. PATENT DOCUMENTS 1,800,300  4/1931  Kränzlein et al. .............. 544/249 X
3,517,005  6/1970  Cronin et al. .................. 544/249 X

OTHER PUBLICATIONS

Sachs, Chemical Abstracts, vol. 3, 1982–1983, (1909).
Komissarov, et al., Chemical Abstracts, vol. 86, 121278f, (1977).

Primary Examiner—Alton D. Rollins
Assistant Examiner—Diana G. Rivers
Attorney, Agent, or Firm—Sprung, Horn, Kramer & Woods

[57] ABSTRACT

The invention includes new 2-amino-3a,4,5,6-tetrahydro-perimidines and method for their preparation from corresponding racemacic compounds. Also included in the invention are pharmaceutical compositions containing said 2-amino-3a,4,5,6-tetrahydro-perimidines and methods for the use of said compounds and compositions.

18 Claims, No Drawings

2-AMINO-3A,4,5,6-TETRAHYDRO-PERIMIDINE DERIVATIVES AND THEIR MEDICINAL USE IN COMBATTING CIRCULATORY DISEASES

The present invention relates to certain new 2-amino-3a,4,5,6-tetrahydro-perimidine derivatives, to a process for their production and to their use as substances having an action on the circulation.

According to the present invention we provide compounds which are 2-amino-3a,4,5,6-tetrahydro-perimidine derivates of the tautomeric formula

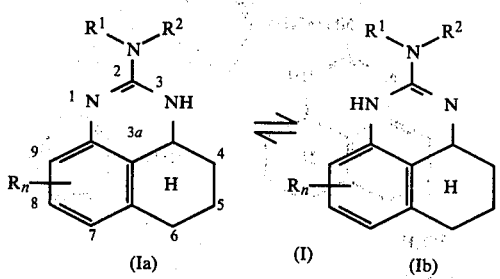

or a salt thereof,
in which
R denotes a hydrogen or halogen atom, n is 1 or 2,
$R^1$ denotes a hydrogen atom or an alkyl or aryl group and
$R^2$ denotes a hydrogen atom or an alkyl, alkenyl, cycloalkyl, aryl, acyl, amino, mono- and di-alkylamino, arylamino or hetero-arylamino group, the aryl radicals mentioned being in turn optionally substituted by halogen, nitro, alkyl, alkoxy (as hereinafter defined), amino or acylamino and the alkyl radicals mentioned being in turn optionally substituted by optionally substituted phenyl, pyridyl or a 5-membered, 6-membered or 7-membered saturated or unsaturated aliphatic ring which can contain 1 or 2 identical or different hetero-atoms selected from oxygen, sulphur and N-R',
in which
R' denotes a hydrogen atom or an alkyl, aryl, aralkyl or acyl group,
or
$R^1$ and $R^2$ together denote an alkylene radical which is optionally interrupted by oxygen or by the group $S(O)_{n'}$ or N—R'';
in which
n' is 0, 1 or 2 and
R'' denotes a hydrogen atom or an alkyl, aryl, heteroaryl, aralkyl or a COR''', CSR''',

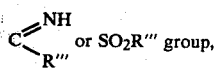 or $SO_2R'''$ group, wherein
R''' denotes an alkyl, cycloalkyl aryl, aralkyl, alkoxy, amino, mono- or di-alkylamino or arylamino group or a 5-membered or 6-membered heterocyclic ring which is saturated or unsaturated and which contains a sulphur atom or 1 or 2 hetero-atoms selected from oxygen, NH and N-alkyl, the aryl radicals mentioned in the definition of R''' being optionally substituted by amino, acylamino, halogen, alkyl, alkoxy, cyano or nitro, in their racemic form or in the form of their optical antipodes.

As used herein the term "alkoxy" when used of radicals or moieties means not only the alkoxy radical itself but also alkenyloxy or cycloalkoxy radicals.

According to the present invention there is further provided a process for the production of a compound of formula (I) in which a 3a,4,5,6-tetrahydro-perimidine of the tautomeric formula

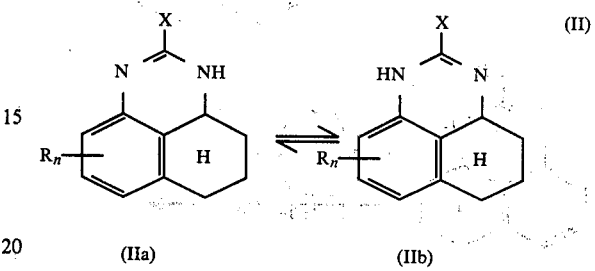

in which
R and n have the meaning indicated above and X denotes a leaving group which can be replaced nucleophilically under the reaction conditions, such as halogen, alkoxy, aryloxy, mercapto, alkylmercapto, arylmercapto, alkylsulphonyl, arylsulphonyl or sulpho, is reacted with an amine of the general formula

in which
$R^1$ and $R^2$ have the meaning indicated above, or with a salt of this amine with an inorganic or organic acid or base in the presence of an inert organic solubilising agent and if appropriate in the presence of an acid-binding agent, at a temperature from 20° C. to 250° C., and, if appropriate, the compound of the formula (I) which still possesses a NH or $NH_2$ group is then acylated, or an $NH_2$ group is produced beforehand by reducing a $NO_2$ group.

Halides of carboxylic acids and sulphonic acids and carbonic acid ester halides, carboxylic acid anhydrides, pyrocarbonic acid esters, isocyanates, isothiocyanates and imido-esters are particularly suitable for this subsequent acylation.

Some reactions are shown by way of example in the equation which follows:

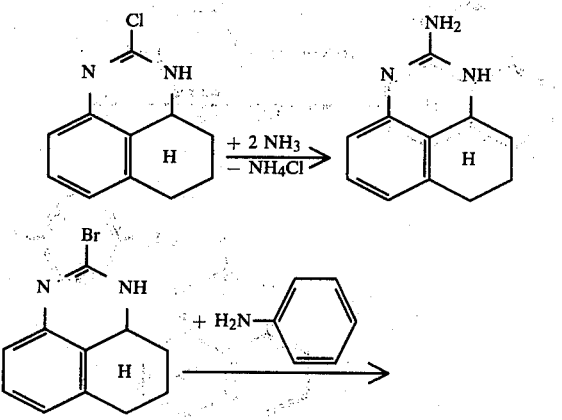

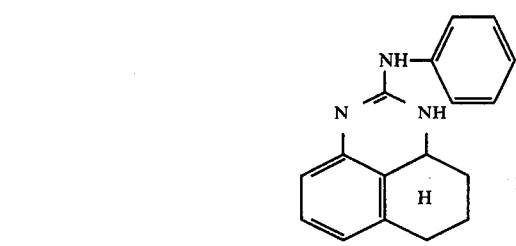
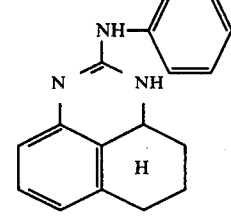
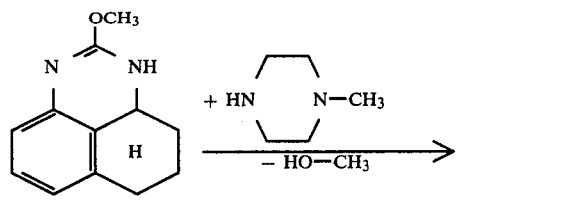
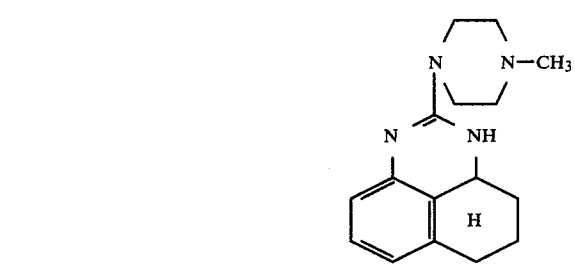
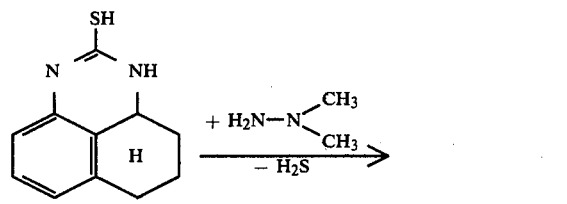
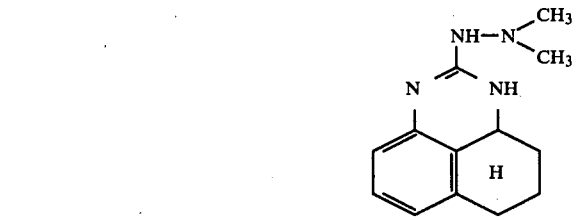
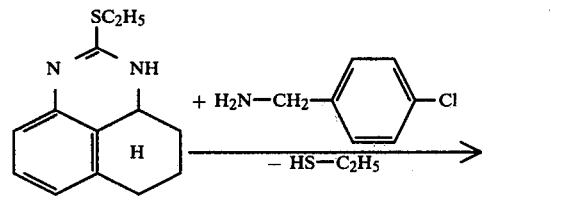
Examples of subsequent acylations of amino groups are:
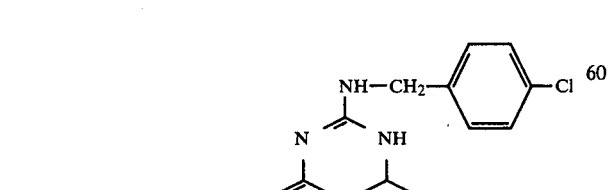
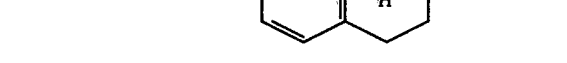

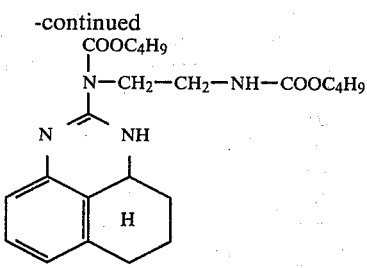

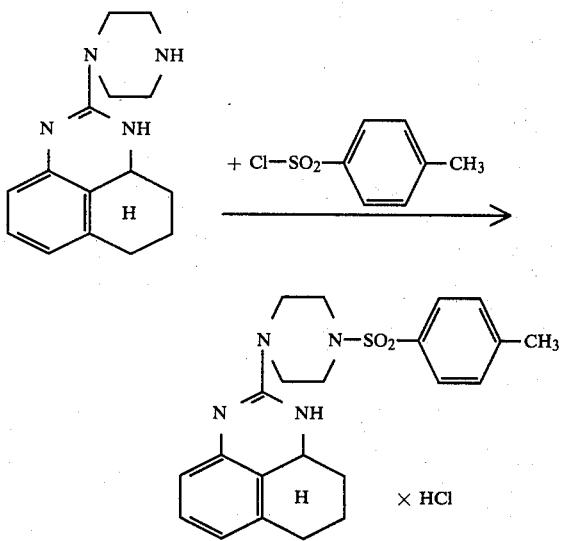

For simplification, in each case only the structure corresponding to the tautomeric formula (Ia) is indicated in the above equations.

In the formulae (I), (II) and (III)

R preferably denotes a hydrogen, chlorine or bromine atom,

R¹ preferably denotes a hydrogen atom, an alkyl group with 1 to 8 carbon atoms, in particular with 1 to 4 carbon atoms, or a phenyl radical and R² preferably denotes a hydrogen atom, an alkyl radical with 1 to 8, in particular 1 to 4, carbon atoms, alkyl radicals mentioned being in turn optionally substituted by phenyl or pyridyl, the phenyl substituent being optionally substituted by a substituent selected from halogen (preferably chlorine) nitro, amino, acylamino (preferably alkanoylamino with 2 to 4 carbon atoms) and alkyl or alkoxy with in each case 1 to 4 (preferably 1 or 2) carbon atoms in the alkyl and alkoxy radical, or R² denotes a phenyl radical, an acyl, preferably an alkanoyl radical with 2 to 4 carbon atoms, an alkenyl radical with up to 4 carbon atoms, a cycloalkyl radical with 3 to 7 carbon atoms, an amino group, a mono- or dialkylamino group with in each case 1 to 4 carbon atoms in the alkyl group(s), a phenylamino radical or a pyridyl-amino radical, or the alkyl groups being optionally substituted by a 5,6- or 7-membered saturated or unsaturated aliphatic ring which can contain one or two identical or different hetero-atoms selected from oxygen, sulphur and N-R', in particular by a piperazino radical which in turn carries R' as a substituent, in which R' denotes a hydrogen atom, an alkyl group with 1 to 4 carbon atoms, a phenyl radical, a benzyl radical or an acyl (preferably alkanoyl) radical with up to 4 carbon atoms, or R¹ and R² together denote an alkylene radical with up to 6 carbon atoms, which is optionally interrupted by oxygen, sulphur, SO₂ or an N-R″ radical, in which R″ denotes a hydrogen atom, an alkyl group with 1 to 4 carbon atoms, a phenyl, naphthyl, benzyl or phenethyl radical or a group COR‴, CSR‴ or

in which

R‴ denotes an alkyl group with 1 to 4 carbon atoms, a cycloalkyl group with 3 to 7 carbon atoms, a phenyl, naphthyl, benzyl or phenethyl radical, an alkoxy group with 1 to 4 carbon atoms, an amino group, a mono- or di-alkylamino group with in each case 1 to 4 carbon atoms in the alkyl radical, a phenylamino or pyridylamino radical or a 5-membered or 6-membered heterocyclic ring which is saturated or unsaturated and which contains a sulphur atom or one or two hetero-atoms selected from oxygen, NH and N-alkyl with 1 to 4 carbon atoms in the alkyl radical, the phenyl, naphthyl and pyridyl radicals mentioned in the definition of R″ being optionally substituted by halogen (preferably chlorine or bromine), nitro, cyano, acylamino (preferably alkanoylamino) with 1 to 4 carbon atoms in the acyl part, alkyl or alkoxy with in each case 1 to 4 carbon atoms.

In formula (II) X preferably denotes a halogen atom, (preferably chlorine or bromine) or a sulpho, alkoxy, alkylmercapto or alkylsulphonyl group.

The alkyl, alkoxy and acyl substituents mentioned preferably contains 1-12, more preferably 1-8 and especially 1-4, carbon atoms. 1-6 carbon atoms are present in the alkyl part of the aralkyl or heterocyclyl-alkyl substituents mentioned.

Aralkyl preferably represents optionally substituted benzyl, phenylethyl or phenylpropyl, and aryl preferably represents optionally substituted phenyl.

Possible substituents in the aryl part of aralkyl or acyl are alkyl, alkoxy, aryloxy, halogen, trifluoromethyl, hydroxyl, alkoxycarbonyl, cyano and nitro.

Hetero-aryl represents 5-membered or 6-membered heterocyclic systems with 1-3 hetero-atoms from the group comprising nitrogen, oxygen and/or sulphur, to which a phenyl ring can also be fused.

The terms aryl or aralkyl, unless otherwise indicated refer to preferably mono- or bi-cyclic carbocyclic aromatic moieties.

The 3a,4,5,6-tetrahydro-perimidines of the tautomeric formula (II) to be used as starting substances can be prepared, for example, by catalytic hydrogenation of known 2-hydroxy-perimidines and subsequent halogenation, in the 2-position, of the products.

Examples which may be mentioned of the starting compounds of the formula (II) are: 2-chloro-3a,4,5,6-tetrahydro-perimidine, 2-bromo-3a,4,5,6-tetrahydro-perimidine, 2-fluoro-3a,4,5,6-tetrahydro-perimidine, 2-iodo-3a,4,5,6-tetrahydro-perimidine, 2-methoxy-3a,4,5,6-tetrahydro-perimidine, 2-ethoxy-3a,4,5,6-tetrahydro-perimidine, 2-isopropoxy-3a,4,5,6-tetrahydro-perimidine, 2-butoxy-3a,4,5,6-tetrahydro-perimidine, 2-benzyloxy-3a,4,5,6-tetrahydro-perimidine, 2-phenyloxy-3a,4,5,6-tetrahydro-perimidine, 2-mercapto-3a,4,5,6-tetrahydro-perimidine, 2-methylmercapto-3a,4,5,6-tetrahydro-perimidine, 2-ethylmercapto-3a,4,5,6-tetrahydro-perimidine, 2-carboxymethylmercapto-3a,4,5,6-tetrahydro-perimidine, 2-benzylmercapto-3a,4,5,6-tetrahydro-perimidine, 2-phenylmercapto-3a,4,5,6-tetrahydro-perimidine, 2-methylsulphonyl-3a,4,5,6-tetrahydro-perimidine, 2-phenylsulphonyl-3a,4,5,6-tetrahydro-perimidine, 2-(4-methyl-phenyl)-sulphonyl-3a,4,5,6-tetrahydro-perimidine, 2-sulpho-3a,4,5,6-tetrahydro-perimidine, 2,7-dichloro-3a,4,5,6-tetrahydro-perimidine, 2,9-dichloro-3a,4,5,6-tetrahydro-perimidine, 2-chloro-7-bromo-3a,4,5,6-tetrahydro-perimidine, 2,7-dibromo-3a,4,5,6-tetrahydro-perimidine, 2,7,9-trichloro-3a,4,5,6-tetrahydro-perimidine, 2-methoxy-7-chloro-3a,4,5,6-tetrahydro-perimidine, 2-mercapto-9-chloro-3a,4,5,6-tetrahydro-perimidine, and 2-benzylmercapto-7-bromo-3a,4,5,6-tetrahydro-perimidine.

The primary and secondary amines or hydrazines of the formula (III) to be used as starting substances are known or can be prepared by known processes.

Possible substituents in alkyl $R^1$ and $R^2$ are hydroxyl, alkoxy, amino, alkylamino, dialkylamino, acylamino, alkoxycarbonyl-amino, trifluoromethyl, cyano, carboxyl, alkoxycarbonyl, aminocarbonyl, alkylaminocarbonyl, dialkylaminocarbonyl, alkylaminocarbonylamino and alkylsulphonyl groups, the alkyl, alkoxy and acyl radicals mentioned in the substituents preferably containing 1-4, in particular 1-2, carbon atoms.

Specific examples which may be mentioned of compounds of the formula (III) are: methylamine, isobutylamine, 2-ethylhexylamine, 4-methylcyclohexylamine, 2-norbornylamine, allylamine, propargylamine, propylenediamine, 1-amino-2-diethylamino-ethane, ethanolamine, 3-ethoxypropylamine, aminoacetic acid ethyl ester, aminopropionitrile, aminoethanesulphonic acid, trifluoromethylethylamine, 2,4-di chlorobenzylamine, 4-chlorophenylethylamine, 3-ethoxyaniline, 4-diethylaminoaniline, 2-aminomethylfurane, 4-aminomethylpyridine, N-aminoethyl-N'-methyl-piperazine, N-aminobutylthiomorpholine 1,1-dioxide, 1-aminomethylisoquinoline, 2-amino-pyridine, 4-aminopyrimidine, 2-aminothiazole, 3-amino-1,2,4-triazole, dimethylamine, methyl-cyclohexylamine, morpholine, thiomorpholine, piperazine, 4-methylpiperazine, 4-phenylpiperazine, 4-fluorophenylpiperazine, 4-(2-chlorophenyl)-piperazine, 4-(2,5-dimethylphenyl)-piperazine, 4-(3,5-dichlorophenyl)-piperazine, 4-aminophenylpiperazine, 4-(fur-2-yl-carbonyl-phenyl)-piperazine, 4-diphenylmethylphenyl-piperazine, 4-(2-phenoxyphenyl)-piperazine, 4-(3-chlorophenyl)-piperazine, 4-ethoxycarbonyl-piperazine, 4-(3-trifluoromethyl)-piperazine, hexamethyleneimine, methylhydrazine, phenylhydrazine, 4-chlorophenylhydrazine, trifluoromethylethylhydrazine, 2-hydrazinopyridine, 4-hydrazinopyrimidine, N,N-dimethylhydrazine, 4-aminomorpholine and 4-aminothiomorpholine 1,1-dioxide.

In the definition of formulae (I) and (III), alkyl, alkenyl and cycloalkyl preferably represent methyl, ethyl, n- and iso-propyl, n-, iso- and tert.-butyl, n- and iso-hexyl, decyl, hexadecyl, allyl, propargyl and cyclohexyl.

Acylamino represents, for example, formylamino, acetylamino, propionylamino, n- and iso-butyrylamino, valerylamino, iso-valerylamino and pivaloylamino.

Alkoxycarbonyl represents, for example, methoxycarbonyl, ethoxycarbonyl, n- and iso-propoxycarbonyl, n-, iso- and tert.-butyoxycarbonyl, allyloxycarbonyl and cyclohexyloxycarbonyl.

Aralkyl represents, for example, benzyl, 4-chlorobenzyl, 2,6-dichlorobenzyl, 3-bromobenzyl, 2-methoxybenzyl, 3-hydroxybenzyl, 2,4,6-trimethylbenzyl, phenylethyl, 4-chlorophenylethyl, phenylpropyl and phenylbutyl.

Aryl represents, for example, phenyl, 2-chlorophenyl, 2,4-dichlorophenyl, 3-nitrophenyl, 3-trifluoromethylphenyl, 2-trifluoromethyl-4-chlorophenyl, 2-methylphenyl, 4-ethylphenyl, 3,4-dimethylphenyl, 3-hydroxyphenyl, 2-methoxyphenyl, 4-ethoxyphenyl, 2-methoxy-5-chlorophenyl, 2,5-diethoxyphenyl, 4-aminosulphonylphenyl, 3-dimethylaminophenyl, 3-ethylaminophenyl and 3-ethylamino-4-methylphenyl.

Hetero-aryl represents, for example, furane, thiophene, pyrrole, oxazole, isoxazole, thiazole, pyrazole, imidazole, triazole, pyridine, pyrimidine, thiazine, indole, benzimidazole, benzoxazole, benzthiazole, indazole, quinoline, isoquinoline, quuinazoline, quinoxaline, benzotriazine and phthalazine.

Alkoxy represents, for example, methoxy, ethoxy, n- and iso-propoxy, n-, iso- and tert.-butoxy, allyloxy and cyclobutoxy.

Alkylamino and dialkylamino represents, for example, methylamino, dimethylamino, ethylamino, diethylamino, methylethylamino, n- and iso-propylamino and n-, iso- and tert.-butylamino.

Those compounds of the formula (I) in which the two substituents $R^1$ and $R^2$, together with the nitrogen atom, form one of the rings which follow are also of interest: pyrrolidino, piperidino, cyclohexylimino, morpholino, thiomorpholino, piperazino, N-methylpiperazino, N-phenylpiperazino, tetrahydroquinolino and 2-methylindolino.

Possible solubilising agents are all the organic solvents which are inert towards the particular reactants. These solvents include, preferably, aliphatic alcohols, for example, alkanots, such as methanol, ethanol, isopropanol or butanol, ethers such as tetrahydrofurane, dioxane, ethylene glycol monomethyl ether and ethylene glycol diethyl ether, glycols, such as ethylene glycol, propylene glycol and diethylene glycol, and corresponding ethers with aliphatic alcohols, such as diethylene glycol dimethyl ether, hydrocarbons, such as ligroin, toluene, xylene and tetralin, halogenated hydrocarbons, such as chloroform, carbon tetrachloride, chlorobenzene and dichlorobenzenes, nitriles, such as acetonitrile and propionitrile, carboxylic acid amides, such as dimethylformamide and dimethylacetamide, heterocyclic bases, such as pyridine, picolines, collidines, quinoline or isoquinoline, and furthermore commercially available industrial mixtures of these solvents.

The reaction can be carried out under normal pressure, but also under increased pressure. Increased pressure can be necessary for the reaction, especially when ammonia or low-boiling primary amines are used as the reactants.

The reaction temperatures can be varied within a substantial range. In general, the reaction is carried out at temperatures between 10° and 250° C., preferably between 20° and 180° C. and in particular between 40° and 150° C.

All the customary acid-binding agents can be employed as the acid-binding agent. These include inorganic bases, such as alkali metal hydroxides and alkaline earth metal hydroxides, for example sodium hydroxide, potassium hydroxide, calcium hydroxide and barium hydroxide, alkali metal carbonates or alkaline earth metal carbonates, such as sodium carbonate, potassium carbonate and calcium carbonate, sodium bicarbonate, potassium bicarbonate and amides, such as sodium amide, as well as organic bases, such as tertiary amines, for example triethylamine, N,N-dimethylaniline, pyridines, quinolines and isoquinolines. An excess of the ammonia, amine or hydrazine reactant can also advantageously be used in the reaction, instead of one of the customary acid-binding agents.

In carrying out the process according to the invention, at least 1 mol of ammonia, amine or hydrazine of the formula (III) and if appropriate at least 1 mol of one of the acid-binding agents mentioned are employed per 1 mol of the 3a,4,5,6-tetrahydro-perimidine of formula (II).

As a rule, the starting substances dissolve completely or partially in the course of the reaction according to the invention, whilst the end products crystallise out. Separating out of the end products can be accelerated by cooling and/or by adding precipitating agents, such as water, lower aliphatic ethers, such as diethyl ether or dibutyl ether, or lower aliphatic hydrocarbons, such as petroleum ether or light petrol.

2-Amino-3a,4,5,6-tetrahydro-perimidine derivatives of the formula (I) in which the group

represents a piperazino or substituted piperazino radical are of particular interest.

Possible substituents in substituted piperazino radicals are $C_1$ to $C_6$ alkyl groups, preferably 1 to 2 methyl groups, on the carbon atoms, and alkyl, aralkyl, heterocyclylalkyl, aryl, hetaryl, acyl, thioacyl, imidoacyl, alkoxycarbonyl, alkylaminocarbonyl, dialkylaminocarbonyl, arylaminocarbonyl, arylaminothiocarbonyl, alkylsulphonyl or arylsulphonyl groups on the 4-N atom.

Examples which may be mentioned of new active compounds are: 2-amino-3a,4,5,6-tetrahydro-perimidine, 2-hydrazino-3a,4,5,6-tetrahydro-perimidine, 2-butylamino-3a,4,5,6-tetrahydro-perimidine, 2-methoxymethylamino-3a,4,5,6-tetrahydro-perimidine, 2-diethylamino-3a,4,5,6-tetrahydro-perimidine, 2-pyrrolidino-3a,4,5,6-tetrahydro-perimidine, 2-hexamethyleneimino-3a,4,5,6-tetrahydro-perimidine, 2-piperazino-3a,4,5,6-tetrahydro-perimidine, 2-(4-methyl)-piperazino-3a,4,5,6-tetrahydro-perimidine, 2-(4-benzyl)-piperazino-3a,4,5,6-tetrahydro-perimidine, 2-(4-phenyl)-piperazino-3a,4,5,6-tetrahydro-perimidine, 2-[4-(4-fluorophenyl)-piperazino]-3a,4,5,6-tetrahydro-perimidine, 2-[4-(2-methoxyphenyl)-piperazino]-3a,4,5,6-tetrahydro-perimidine, 2-[4-(3,4-dichlorophenyl)-piperazino]-3a,4,5,6-tetrahydroperimidine, 2-[4-(4-cyclohexylphenyl)-piperazino]-3a,4,5,6-tetrahydro-perimidine, 2-[4-(3-trifluoromethylphenyl)-piperazino]-3a,4,5,6-tetrahydro-perimidine, 2-[4-(2,5-dimethylphenyl)-piperazino]-3a,4,5,6-tetrahydro-perimidine, 2-[4-(4-hydroxyphenyl)-piperazino]-3a,4,5,6-tetrahydro-perimidine, 2-[4-(4-tert.-butylphenyl)-piperazino]-3a,4,5,6-tetrahydro-perimidine, 2-[4-(4-chlorophenyl)-piperazino]-3a,4,5,6-tetrahydro-perimidine, 2-(4-acetyl)-piperazino-3a,4,5,6-tetrahydro-perimidine, 2-(4-benzoyl)-piperazino-3a,4,5,6-tetrahydro-perimidine, 2-(4-fur-2-yl-carbonyl)-piperazino-3a,4,5,6-tetrahydro-perimidine, 2-(4-phenyl)-piperazino-7-chloro-3a,4,5,6-tetrahydro-perimidine, 2-(4-phenyl)-piperazino-9-chloro-3a,4,5,6-tetrahydro-perimidine, 2-(4-phenyl)-piperazino-7,9-dichloro-3a,4,5,6-tetrahydro-perimidine, 2-(4-thiobenzoyl)-piperazino-3a,4,5,6-tetrahydro-perimidine, 2-(4-phenylimidoacyl)-piperazino-3a,4,5,6-tetrahydro-perimidine, 2-[4-(4-ethylsulphonyl)-phenyl]-piperazino-3a,4,5,6-tetrahydro-perimidine, 2-(4-chlorobenzoyl)-piperazino-3a,4,5,6-tetrahydro-perimidine, 2-(4-phenylaminocarbonyl)-piperazino-3a,4,5,6-tetrahydro-perimidine, 2-(4-phenylaminothiocarbonyl)-piperazino-3a,4,5,6-tetrahydro-perimidine, 2-phenylamino-3a,4,5,6-tetrahydro-perimidine, 2-(4-chlorophenylamino)-3a,4,5,6-tetrahydro-perimidine, 2-(2-ethoxycarbonylphenyl)-piperazino-3a,4,5,6-tetrahydro-perimidine, 2-(4-chlorophenyl)-methylamino-3a,4,5,6-tetrahydro-perimidine, 2-morpholinopropylamino-3a,4,5,6-tetrahydro-perimidine, 2-(4-methylpiperazino)-propylamino-3a,4,5,6-tetrahydro-perimidine, 2-(2-pyridylmethyl)-amino-3a,4,5,6-tetrahydro-perimidine, 2-(4-pyrimidylmethyl)-amino-3a,4,5,6-tetrahydro-perimidine, 2-(2-pyridylethyl)-amino-3a,4,5,6-tetrahydro-perimidine, 2-(2-quinolylmethyl)-amino-3a,4,5,6-tetrahydro-perimidine, 2-phenylhydrazino-3a,4,5,6-tetrahydro-perimidine, 2-(4-chlorophenyl)-hydrazino-3a,4,5,6-tetrahydro-perimidine, 2-dimethylhydrazino-3a,4,5,6-tetrahydro-perimidine, 2-(2-pyridyl)-hydrazino-3a,4,5,6-tetrahydro-perimidine, 2-(4-pyrimidyl)-hydrazino-3a,4,5,6-tetrahydro-perimidine, 2-acetylamino-3a,4,5,6-tetrahydro-perimidine, 2-butyrylamino-3a,4,5,6-tetrahydro-perimidine, 2-phenylacetylamino-3a,4,5,6-tetrahydro-perimidine, 2-(4-chlorophenylacetyl)-amino-3a,4,5,6-tetrahydro-perimidine, 2-(3-chlorobenzoyl)-amino-3a,4,5,6-tetrahydro-perimidine, 2-ethoxycarbonylamino-3a,4,5,6-tetrahydro-perimidine, 2-propoxycarbonylamino-3a,4,5,6-tetrahydro-perimidine, 2-dimethylaminocarbonylamino-3a,4,5,6-tetrahydro-perimidine, 2-methylaminocabonylamino-3a,4,5,6-tetrahydro-perimidine, 2-ethylsulphonylamino-3a,4,5,6-tetrahydro-perimidine 2-(2-chloroethylsulphonyl)-amino-3a,4,5,6-tetrahydro-perimidine, 2-(2-chloroethylsulphonyl)-amino-3a,4,5,6-tetrahydro-perimidine, 2-phenylsulphonylamino-3a,4,5,6-tetrahydro-perimidine and 2-(4-methylsulphonyl-amino-3a,4,5,6-tetrahydro-perimidine.

The new active compounds can be both in the form of the tautomeric formulae Ia and/or Ib and, in the case where $R^1$ represents hydrogen, in the corresponding tautomeric 2-imino forms. Furthermore, they can be used in the form of their optical antipodes, in the pure D-form or L-form and also as racemates.

Racemate mixtures can be separated into the pure racemates in a known manner on the basis of the physicochemical differences of the constituents, for example by chromatography and/or fractional crystallisation.

Pure racemates can be resolved according to known methods, for example by recrystallisation from an optically active solvent, with the aid of micro-organisms or by reaction with an optically active acid or base which forms salts with the racemic compound and separation of the salts obtained in this manner, for example on the basis of their different solubilities, into the diastereomers from which the antipodes can be liberated by the action of suitable agents. Particularly customary optically active acids are, for example, the d- and l-forms of tartaric acid, di-o-toluyltartaric acid, malic acid, mandelic acid, camphorsulphonic acid or quinic acid. Suitable optically active bases are, for example, optically active α-phenylethylamine, α-(1-naphthyl)-ethylamine, quinine, cinchonidine and brucine. Advantageously, the more active of the two antipodes is isolated.

According to the invention it is however also possible to obtain the end products in the form of the pure racemates or optical antipodes by employing starting substances, containing one or more asymmetrical C atoms, in the form of the pure racemates or optical antipodes.

The new compounds can be used as medicaments, in particular as substances having an influence on the circulation.

The compounds according to the invention have a broad and diverse pharmacological action spectrum.

In detail, the compounds according to the invention display the following main actions:

1. The new compounds lower the blood pressure of hypertonic animals and can thus be used as anti-hypertensive agents.

2. On isolated hearts through which blood flows, the new compounds produce a distinct and long-lasting dilation of the coronary vessels.

3. The tone of the smooth muscle of the vessels is greatly reduced under the action of the compounds. This vascular-spasmolytic action can take place in the entire vascular system or can manifest itself more or less isolated in circumscribed bascular regions (such as, for example, in the muscle and in the central nervous system, inter alia).

4. The compounds have muscular-spasmolytic actions which manifest themselves on the smooth muscle of the stomach, the intestinal tract, the urogenital tract and the respiratory tract.

The new compounds are accordingly suitable for preventing, alleviating or curing diseases for which, in particular, the effects indicated above are desired.

As stated above, the invention also relates to the use in medicine of the compounds of the invention.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, bloodisotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for parenteral (intravenous) administration of the medicaments of the invention is 2.5 to 500 mg of active ingredient, and for oral administration the preferred daily dose is 50 mg to 2.5 g.

The product of the above-mentioned pharmaceutical compositions and medicaments is carried out by any method known in the art, for example, by mixing the active ingredient(s) with the diluent(s) to form a pharmaceutical compositions (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally and parenterally, especially perlingually and intravenously. Preferred pharmaceutical compositions and medicaments are therefore those adapted for administration such as oral and parenteral administration. Administration in the method of the invention is preferably oral and parenteral administration.

In general it has proved advantageous to administer parenterally amounts of from 0.01 mg to 50 mg/kg, preferably 0.05 mg to 10 mg/kg, of body weight per day and to administer orally 0.1 mg to 200 mg/kg, preferably 1 to 50 mg/kg, of body weight per day, to achieve effective results. An individual administration preferably contains amounts of 0.01 mg to 20 mg/kg, more preferably 0.1 mg to 2 mg/kg, of body weight. Nevertheless, it can at times be necessary to deviate from those dosage rates, and in particular to do so as a function of the nature and body weight of the warm blooded animal subject to be treated, the individual reaction of this subject of the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The present invention also includes those medicaments which additionally contain further active compounds, besides compounds of the formula (I). Other active compounds which may be mentioned are, preferably: saluretic agents, diuretic agents, other active compounds having an influence on the circulation, psychotherapeutic agents and analgesic agents.

The following Examples illustrate the preparation of individual compounds of the invention.

EXAMPLE 1

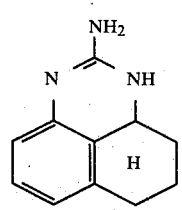

62 g (0.3 mol) of 2-chloro-3a,4,5,6-tetrahydroperimidine in 400 ml of ethanol and 150 ml of liquid ammonia are heated to 150° in an autoclave for 6 hours. The pressure thereby increases to a maximum of 30 bars. After cooling, the reaction mixture is evaporated to dryness. The residue is dissolved in water, the solution is filtered through active charcoal and the 2-amino-3a,4,5,6-tetrahydroperimidine formed is precipitated by adding aqueous ammonia. After filtering off and drying the product, 40 g (71% of theory) of melting point 230°-232° are obtained. Preparation of 2-chloro-3a,4,5,6-tetrahydro-perimidine:

(a) An autoclave is charged with 368 g (2 mols) of perimid-2-one, 900 ml of tetrahydrofurane, 500 ml of water and 75 g of Raney nickel. After displacing the air with nitrogen, the mixture introduced is charged with hydrogen up to a pressure of 100 bars and is heated to 175° C., whilst stirring. As soon as this temperature is reached, the hydrogen pressure is increased to 150 bars and is maintained at this value throughout the entire reaction time by adding hydrogen at the rate at which it is consumed. After the absorption of hydrogen has ended, the mixture is stirred for a further hour under the abovementioned hydrogenation conditions in order to bring the reaction to completion and is then cooled to room temperature and let down to normal pressure. 500 ml of dimethylformamide are added and the reaction mixture is warmed to 60° to 75° C. and separated off from the catalyst, whilst warm, by filtration. The reaction solution obtained as the filtrate is cooled to 0° to 10° C., whereupon some of the reaction product precipitates in the pure crystalline form, and is separated off. The mother liquor is then evaporated down to a volume of about 700 ml and 700 ml of water are added to the residue, whereupon further reaction product precipitates. A total of 342 g of 2-hydroxy-3a,4,5,6-tetrahydroperimidine of melting point 230°-233° C. are obtained. Yield: 90% of theory.

(b) 100 g (0.53 mol) of 2-hydroxy-3a,4,5,6-tetrahydroperimidine in 500 ml of phosphorus oxychloride are heated to 110° (reflux temperature) for 5 hours. Towards the end of the reaction time, a clear solution is formed, with vigorous evolution of HCl, and is cooled to about 60°. After adding 1,000 ml of carbon tetrachloride, the mixture is stirred further, whilst cooling with ice, whereupon the hydrochloride of the 2-chloro-3a,4,5,6-tetrahydro-perimidine formed (melting point 182°–185°) crystallises out. After filtering off and washing the product with carbon tetrachloride, it is stirred into a mixture of excess ammonia and ice and the free base is allowed to crystallise out for about 1 hour, whilst stirring occasionally and adding further ice. This base is filtered off and washed with water. Yield: 94 g (86% of theory) of melting point 144°–146°.

EXAMPLE 2

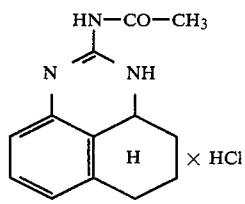

3.7 g (0.02 mol) of the reaction product from Example 1 in 10 ml of glacial acetic acid are heated to 115° C. (reflux temperature) with 4.1 g (0.04 mol) of acetic anhydride for 8 hours. After cooling, the solution is evaporated to dryness and the residue is stirred with 10% strength ethanolic hydrochloric acid. After filtering off and washing with ethanol, 1.9 g (38% of theory) of 2-acetylamino-3a,4,5,6-tetrahydro-perimidine hydrochloride of melting point 229°–230° C. are obtained.

EXAMPLE 3

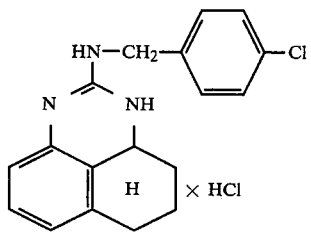

10.3 g (0.05 mol) of 2-chloro-3a,4,5,6-tetrahydroperimidine and 7.1 g (0.05 mol) of 4-chloro-benzylamine in 100 ml of ethanol are heated to 80° C. for 1 hour. After cooling, the crystals which have precipitated are filtered off and purified by dissolving in hot ethanol and precipitating with water. 2-(4-Chlorobenzylamino)-3a,4,5,6-tetrahydro-perimidine hydrochloride is obtained. Yield: 10 g (57.5% of theory) of melting point 257°–258° C.

EXAMPLE 4

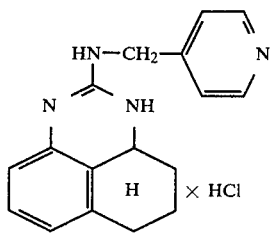

8.5 g (54% of theory) of 2-(4-pyridylmethylamino)-3a,4,5,6-tetrahydro-perimidine hydrochloride of melting point 228°–230° C. (from ethanol) are obtained analogously to Example 3, in the course of 2 hours at 80° C., from 10.3 g (0.05 mol) of 2-chloro-3a,4,5,6-tetrahydroperimidine and 5.9 g (0.055 mol) of 4-aminomethylpyridine in 50 ml of ethanol.

EXAMPLE 5

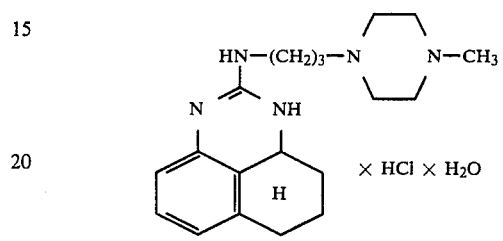

10.3 g (0.05 mol) of 2-chloro-3a,4,5,6-tetrahydroperimidine and 8.6 g (0.055 mol) of N-methyl-N'-aminopropylpiperazine in 50 ml of acetone are heated to 55° C. for 2 hours. After cooling, 50 ml of ether are added and the reaction mixture is placed in a refrigerator for 24 hours. The crystals which have precipitated are filtered off and rinsed with ether. 10.6 g (55.6% of theory) of 2-(4-methylpiperazinopropylamino)-3a,4,5,6-tetrahydro-perimidine hydrochloride hydrate are thereby obtained. Melting point 155°–157° C.

EXAMPLE 6

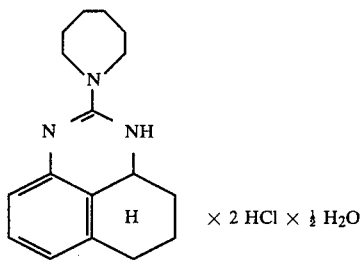

20.6 g (0.1 mol) of 2-chloro-3a,4,5,6-tetrahydroperimidine and 10.9 g (0.11 mol) of hexamethyleneimine in 100 ml of ethanol are heated to 80° C. for 1.5 hours. After cooling, 100 ml of petroleum ether are added and the crystals formed are isolated by filtration. For purification, the product is dissolved in warm water, the solution is filtered through active charcoal, and excess hydrochloric acid is added to the filtrate. 2-Hexamethyleneamino-3a,4,5,6-tetrahydro-perimidine dihydrochloride hemihydrate thereby crystallises out. Yield: 12.2 g (35% of theory) of melting point 277°–280° C.

EXAMPLE 7

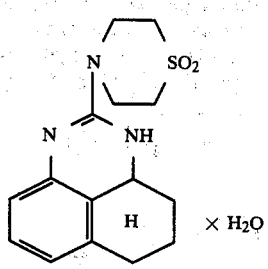

15.3 g of 2-(tetrahydro-1,4-thiazino-1,1-dioxide)-3a,4,5,6-tetrahydro-perimidine hydrochloride are obtained analogously to Example 3, in the course of 2 hours at 100° C., from 10.3 g (0.05 mol) of 2-chloro-3a,4,5,6-tetrahydroperimidine and 7.4 g (0.055 mol) of tetrahydro-1,4-thiazine 1,1-dioxide in 50 ml of dioxane. When the hydrochloride is made into a slurry with dilute sodium hydroxide solution, the hydrate of the free base is formed. Yield: 11.4 g (71% of theory) of melting point 228°–230° C.

EXAMPLE 8

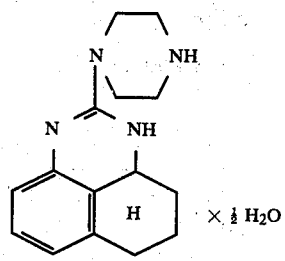

103 g (0.5 mol) of 2-chloro-3a,4,5,6-tetrahydroperimidine and 485 g (2.5 mols) of piperazine hexahydrate in 1,000 ml of isopropanol are heated to 80° C. (reflux temperature) for 1 hour. After cooling, the reaction mixture is evaporated to dryness on a Rotavapor. Dilute sodium hydroxide solution is added to the residue, and the oil which has separated out is taken up in methylene chloride. After drying over sodium sulphate, evaporating the solution and stirring the residue with ethyl acetate, 2-piperazino-3a,4,5,6-tetrahydro-perimidine hemihydrate crystallises out. Yield: 85 g (66% of theory) of melting point 170°–172° C.

EXAMPLE 9

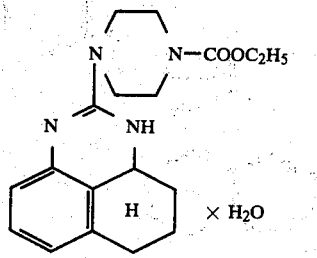

8.1 g (0.05 mol) of pyrocarbonic acid diethyl ester are added dropwise to 12.8 g (0.05 mol) of the reaction product from Example 8 in 50 ml of ethanol, whilst stirring. The temperature rises to 35° C., with vigorous evolution of $CO_2$. After 7 hours, the reaction mixture is evaporated on a Rotavapor, water is added to the residue and the 2-(4-ethoxycarbonylpiperazino)-3a,4,5,6-tetrahydro-perimidine hydrate formed is isolated by filtration. Yield: 13.8 g (80% of theory) of melting point 137°–139° C. (from ethanol).

EXAMPLE 10

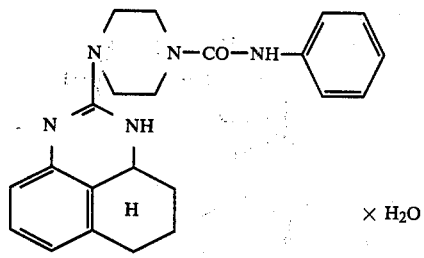

6.5 g (0.055 mol) of phenyl isocyanate are added dropwise to 12.8 g (0.05 mol) of the reaction product from Example 8 in 50 ml of pyridine at 0°–5° C. (cooling with ice). The mixture is stirred at room temperature for 10 hours, the solvent is evaporated off on a Rotavapor, water is added to the residue and, after leaving the mixture to stand for 12 hours, 2-(4-phenylaminocarbonylpiperazino)-3a,4,5,6-tetrahydro-perimidine hydrate is isolated by filtration. The compound is obtained in an analytically pure form by washing with acetone. Yield: 6.5 g (33% of theory) of melting point 202°–205° C.

EXAMPLE 11

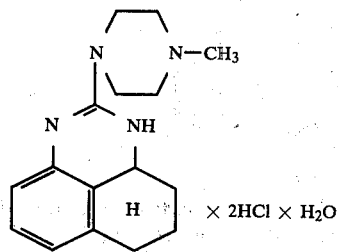

25.5 g (71% of theory) of 2-(4-methylpiperazino)-3a,4,5,6-tetrahydro-perimidine dihydrochloride hydrate are obtained analogously to Example 3, in the course of 30 minutes at 100° C., from 20.6 g (0.1 mol) of 2-chloro-3a,4,5,6-tetrahydro-perimidine and 11 g (0.11 mol) of N-methylpiperazine in 100 ml of methyl isobutyl ketone. Melting point 322°–324° C.

EXAMPLE 12

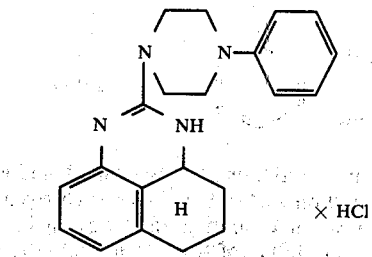

42 g (76% of theory) of 2-(4-phenylpiperazino)-3a,4,5,6-tetrahydro-perimidine hydrochloride are obtained analogously to Example 3, in the course of 1 hour at 65° C., from 30.9 g (0.15 mol) of 2-chloro-3a,4,5,6-tetrahydroperimidine and 24.3 g (0.15 mol) of N-phenyl-piperazine in 100 ml of tetrahydrofurane. Melting point 296°–297° C.

EXAMPLE 13

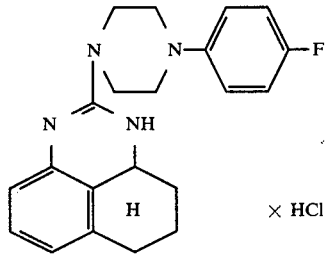

14.3 g (82% of theory) of 2-[4-(4-fluorophenyl)-piperazino]-3a,4,5,6-tetrahydro-perimidine hydrochloride are obtained analogously to Example 3, in the course of 1 hour at 80° C., from 9.36 g (0.045 mol) of 2-chloro-3a,4,5,6-tetrahydroperimidine and 9 g (0.05 mol) of N-(4-fluorophenyl)-piperazine in 50 ml of ethanol. Melting point: 290°–293° C.

EXAMPLE 14

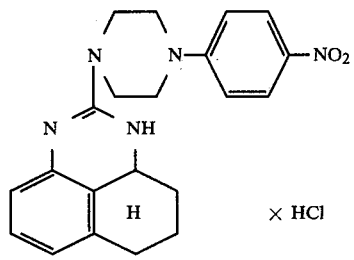

102 g (85% of theory) of 2-[4-(4-nitrophenyl)-piperazino]-3a,4,5,6-tetrahydro-perimidine hydrochloride are obtained analogously to Example 3, in the course of 2 hours at 60° C., from 59.8 g (0.29 mol) of 2-chloro-3a,4,5,6-tetrahydro-perimidine and 60.4 g (0.32 mol) of N-(4-nitrophenyl)-piperazine in 500 ml of methanol. Melting point: 345° C., decomposition.

EXAMPLE 15

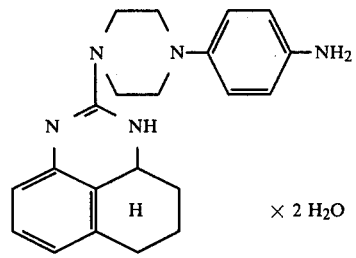

75 g (0.18 mol) of the reaction product from Example 14 in 350 ml of dimethylformamide are hydrogenated at 50° C. in the presence of 15 g of Raney nickel in the course of 3 hours. 100 ml of 10% strength hydrochloric acid are added to the reaction mixture, the catalyst is filtered off, whilst warm, and the filtrate is evaporated to dryness on a Rotavapor. By making the residue into a slurry with dilute aqueous ammonia and filtering off the solid and washing it with water, 2-[4-(4-aminophenyl)-piperazino]-3a,4,5,6-tetrahydro-perimidine dihydrate is obtained. Yield: 39.7 g (57.6% of theory) of melting point 305° C.

EXAMPLE 16

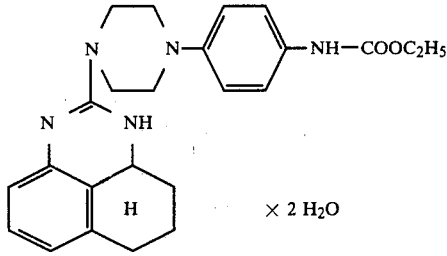

8.6 g (94.5% of theory) of 2-[4-(4-ethoxycarbonylaminophenyl)-piperazino]-3a,4,5,6-tetrahydroperimidine dihydrate are obtained analogously to Example 9, in the course of 6 hours at 80° C., from 7.7 g (0.02 mol) of the reaction product from Example 15 and 6.48 g (0.04 mol) of pyrocarbonic acid diethyl ester. Melting point: 280°–282° C.

EXAMPLE 17

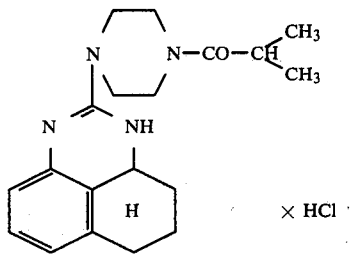

15 g (83% of theory) of 2-(4-isobutyrylpiperazino)-3a,4,5,6-tetrahydro-perimidine hydrochloride are obtained analogously to Example 6, in the course of 1 hour at 80° C., from 10.3 g (0.05 mol) of 2-chloro-3a,4,5,6-tetrahydroperimidine and 8.58 g (0.055 mol) of N-isobutyrylpiperazine in 50 ml of ethanol. Melting point: 295°–297° C.

EXAMPLE 18

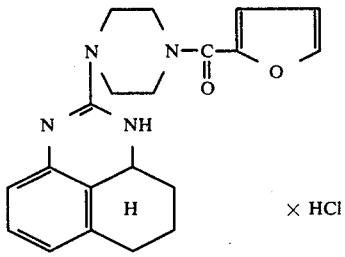

17.2 g (90.7% of theory) of 2-(4-fur-2-yl-carbonyl-piperazino)-3a,4,5,6-tetrahydro-perimidine hydrochloride are obtained analogously to Example 3, in the course of 30 minutes at 90° C., from 10.3 g (0.05 mol) of 2-chloro-3a,4,5,6-tetrahydro-perimidine and 9.9 g (0.055 mol) of N-fur-2-yl-carbonyl-piperazine in 80 ml of n-propanol. Melting point: 299°–300° C.

EXAMPLE 19

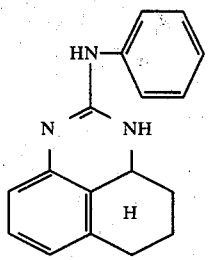

10.3 g (0.05 mol) of 2-chloro-3a,4,5,6-tetrahydroperimidine are introduced into 15 ml of aniline, whilst stirring. After the strongly exothermic reaction has subsided (temperature rises to 90° C.), water is added to the mixture and the crystals which have precipitated are isolated by filtration and washed several times with dilute aqueous ammonia solution. 2-Phenylamino-3a,4,5,6-tetrahydro-perimidine is obtained. Yield: 9.5 g (72% of theory) of melting point 233°–235° C.

EXAMPLE 20

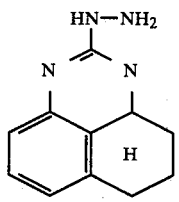

61.8 g (0.3 mol) of 2-chloro-3a,4,5,6-tetrahydroperimidine are heated to 80° C. with 19.2 g (0.6 mol) of anhydrous hydrazine in 250 ml of ethanol for 4 hours. After cooling the mixture, 250 ml of petroleum ether are added and the crystals formed are isolated by filtration. 2-Hydrazino-3a,4,5,6-tetrahydro-perimidine is obtained. Yield: 54 g (89% of theory) of melting point 191°–193° C.

EXAMPLE 21

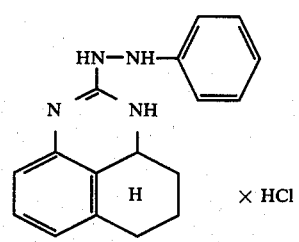

11 g (70% of theory) of 2-phenylhydrazino-3a,4,5,6-tetrahydro-perimidine hydrochloride are obtained analogously to Example 6, in the course of 1 hour at 80° C. and after precipitation with petroleum ether, from 10.3 g (0.05 mol) of 2-chloro-3a,4,5,6-tetrahydro-perimidine and 8.1 g (0.075 mol) of phenylhydrazine in 100 ml of ethanol. Melting point: 243°245° C.

EXAMPLE 22

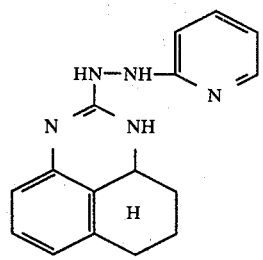

20.6 g (0.1 mol) of 2-chloro-3a,4,5,6-tetrahydroperimidine and 12 g (0.11 mol) of 2-hydrazinopyridine in 100 ml of methanol are heated to 60° C. for 1 hour. After cooling the mixture, ice-water is allowed to run in and the 2-(2-pyridylhydrazino)-3a,4,5,6-tetrahydro-perimidine formed is precipitated by means of dilute sodium hydroxide solution. After filtering off the precipitate and washing it with water, a crude product results, which is obtained in the analytically pure form by washing with ethyl acetate. Yield: 22.5 g (81% of theory) of melting point 205°–207° C.

EXAMPLE 23

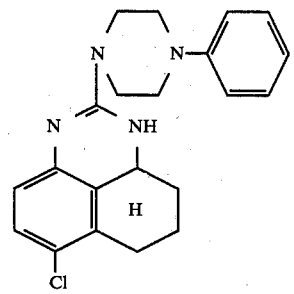

17.5 g of 2-(4-phenyl)-piperazino-7-chloro-3a,4,5,6-tetrahydro-perimidine hydrochloride of melting point 290°–291° C. are obtained analogously to Example 3, in the course of 1 hour at 80° C., from 12.1 g (0.05 mol) of 2,7-dichloro-3a,4,5,6-tetrahydro-perimidine (melting point: 190°–192° C.) and 8.1 g (0.05 mol) of N-phenyl-piperazine in 50 ml of ethanol. By dissolving the product in a mixture of acetone and aqueous ammonia and precipitation with water, 15.3 g (83% of theory) of the base of melting point 178°–179° C. are obtained.

EXAMPLE 24

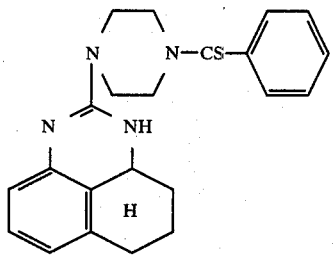

8.6 g (0.033 mol) of the reaction product from Example 8 and 6 g of dithiobenzoic acid methyl ester in 15 ml of 1,2-dichlorobenzene are heated to 150° C. for 1 hour, whereupon methylmercaptan is evolved. After about 30 minutes, a precipitate is formed which, after cooling to 25° C., is filtered off, ether being added. 7 g (56% of theory) of 2-(4-thiobenzoyl)-piperazino-3a,4,5,6-tetrahydro-perimidine of melting point 230°–232° C. are obtained.

EXAMPLE 25

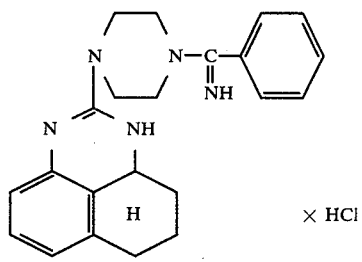

× HCl

A mixture of 6.4 g (0.025 mol) of the reaction product from Example 8, 15 ml of xylene and 4.5 g of iminobenzoic acid methyl ester hydrochloride is heated to 145° C. for 6 hours and cooled and the reaction product is filtered off, ether being added. 7 g (66% of theory) of 2-(4-phenylimidoacyl)-piperazino-3a,4,5,6-tetrahydroperimidine hydrochloride of melting point 230° C. (decomposition) are thereby formed.

EXAMPLE 26

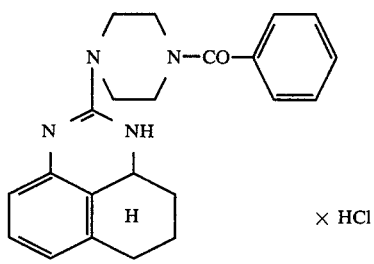

× HCl 7.7 g (0.055 mol) of benzoyl chloride are added dropwise to 12.8 g (0.05 mol) of the reaction product from Example 8 in 150 ml of pyridine at 0°–5° C. (cooling with ice). The mixture is allowed to come to room temperature and is then heated to 60° C. for 5 hours. The solvent is distilled off in vacuo and water is added to the residue, whereupon 2-(4-benzoyl)-piperazino-3a,4,5,6-tetrahydroperimidine hydrochloride crystallises out. After filtering off and washing with water, 10 g (50% of theory) of product of melting point 295°–297° C. are obtained.

EXAMPLE 27

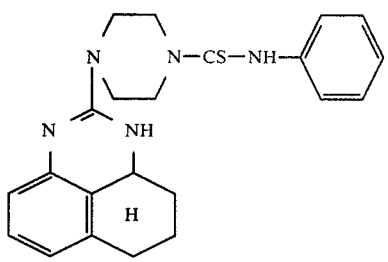

16.1 g (82% of theory) of 2-(4-phenylaminothiocarbonyl)-piperazino-3a,4,5,6-tetrahydro-perimidine of melting point 236°–238° C. are obtained analogously to Example 10, at 20°–25° C. in the course of 10 hours, from 12.8 g (0.05 mol) of the reaction product from Example 8 and 7.5 g (0.055 mol) of phenyl isothiocyanate in 100 ml of pyridine.

Among the new 2-amino-3a,4,5,6-tetrahydroperimidine salts of the invention, those salts that are pharmaceutically acceptable are particularly important and are preferred.

The new free 2-amino-3a,4,5,6-tetrahydroperimidines of the general formula I and their salts can be interconverted in any suitable manner; methods for such interconversion are known in the art.

The present invention also comprises pharmaceutically acceptable bioprecursors of the active compounds of the present invention.

For the purposes of this Specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A 2-amino-3a,4,5,6-tetrahydroperimidine derivative of the tautomeric formulae

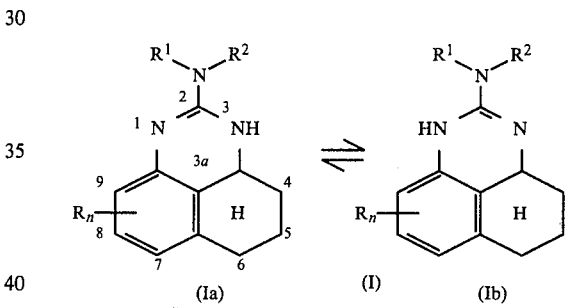

or a salt thereof,
in which
R denotes a hydrogen or halogen atom, n is 1 or 2,
$R^1$ denotes a hydrogen atom or a $C_1$–$C_8$—alkyl group or a phenyl group and
$R^2$ denotes a hydrogen atom or a $C_1$–$C_8$—alkyl group which is optionally substituted by a 5-membered or 6-membered saturated or unsaturated aliphatic ring which can contain 1 or 2 identical or different N—R′ groups,
in which
R′ denotes a hydrogen atom, a $C_1$–$C_4$-alkyl group, a benzyl group, an alkanoyl group having up to 4 carbon atoms, or a benzyl, phenethyl, phenylpropyl, phenyl or chlorophenyl group,
or
$R^1$ and $R^2$ together denote an alkylene group having up to 6 carbon atoms which is optionally interrupted by oxygen or by the group $S(O)_n$, or N-R″ which together with the nitrogen atom form a 5-or 6-membered ring
in which
n′ is 0, 1 or 2 and
R″ denotes a hydrogen atom or a $C_1$—$C_4$—alkyl group, a phenyl, fluorophenyl, naphthyl, benzyl or phenethyl group, or a —COR‴, CSR‴,

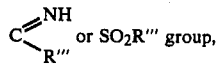 or SO$_2$R''' group, wherein
R''' denotes a C$_1$-C$_4$—alkyl group, a C$_3$-C$_7$ cycloalkyl group; a phenyl, naphthyl, benzyl or phenethyl group optionally substituted by halogen, nitro, cyano, C$_1$-C$_4$—acylamino, C$_1$-C$_4$-alkyl or C$_1$-C$_4$-alkoxy, a C$_1$-C$_4$-alkoxy group, an amino, mono- or di-alkylamino with 1 to 4 carbon atoms in each alkyl group, or a phenylamino group optionally substituted by amino, C$_1$-C$_4$-acylamino, halogen, C$_1$-C$_4$-alkyl, C$_1$-C$_4$-alkoxy, cyano or nitro.

2. A compound according to claim 1 or a salt thereof wherein

denotes the group

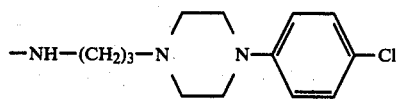

or the group

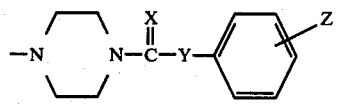

in which
X is O, S or NH
Y is a valence bond or the group NH and
Z denotes H, Cl or OR,
wherein
R is C$_1$-C$_4$-alkyl.

3. A compound according to claim 1 in which
R denotes a hydrogen or chlorine atom,
R$^1$ denotes a hydrogen atom or a C$_1$-C$_8$-alkyl group and
R$^2$ denotes a hydrogen atom or a C$_1$-C$_8$-alkyl group optionally substituted by a 5-membered or 6-membered saturated or unsaturated aliphatic ring which can contain 1 or 2 identical or different N—R' groups,
in which
R' denotes a hydrogen atom or phenyl group, or
R$^1$ and R$^2$ together denote a alkylene group having up to 6 carbon atoms, which is optionally interrupted by an N-R'' group which together with the nitrogen atom form a 5- or 6-membered ring
in which
n' is 0, 1 or 2 and R'' denotes a hydrogen atom, a phenyl group or a group COR''',

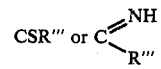

in which
R''' denotes a phenyl group optionally substituted by halogen, nitro, cyano, C$_1$-C$_4$-acylamino, C$_1$-C$_4$-alkyl or C$_1$-C$_4$-alkoxy.

4. A compound according to claim 1 or a salt thereof wherein R$^1$ and R$^2$ together denote a piperazinyl, piperidinyl, cyclohexyl or cyclohexenyl group.

5. A compound according to claim 2, or a salt thereof, in which R'' is substituted by a chlorine or bromine atom.

6. 2-Piperazino-3a,4,5,6-tetrahydro-perimidine.

7. 2-(Phenyl)-piperazino-3a,4,5,6-tetrahydroperimidine.

8. 2-[4-(4-Fluorophenyl)-piperazino]-3a,4,5,6-tetrahydro-perimidine.

9. 2-(4-Fur-2-yl-carbonyl)-piperazino-3a,4,5,6-tetrahydro-perimidine.

10. A pharmaceutical composition containing as an active ingredient an antihypertensively effective amount of a compound according to claim 1 in admixture with a solid or liquefied gaseous diluent or in admixture with a liquid diluent other than a solvent of a molecular weight less than 200 except in the presence of a surface-active agent.

11. A pharmaceutical composition of claim 10 in the form of a sterile or isotonic aqueous solution.

12. A composition according to claim 10 or 11 containing from 0.5 to 95% by weight of the said active ingredient.

13. A medicament in dosage unit form comprising an antihypertensively effective amount of a compound according to claim 1 together with an inert pharmaceutical carrier.

14. A medicament of claim 13 in the form of tablets, pills, dragees, capsules, ampoules, or suppositories.

15. A method of combating circulatory diseases in warm-blooded animals which comprises administering to said animals an antihypertensively effective amount of an active compound according to claim 1 either alone or in admixture with a diluent or in the form of a medicament.

16. A method according to claim 15 in which the active compound is administered parenterally in an amount of 0.01 to 50 mg per kg body weight per day, or orally in an amount of 0.1 to 200 mg per kg body weight per day.

17. A method according to claim 16 in which the active compound is administered parenterally in an amount of 0.05 mg to 10 mg per kg body weight per day, or orally in an amount of 1 to 50 mg per kg body weight per day.

18. A compound according to claim 1, in which n=1 and R'' has the same meaning as in claim 1.

* * * * *

UNITED STATES PATENT AND TRADEMARK OFFICE
CERTIFICATE OF CORRECTION

PATENT NO. : 4,328,223
DATED : May 4, 1982
INVENTOR(S) : Hans-Joachim Kabbe, et al.

It is certified that error appears in the above-identified patent and that said Letters Patent are hereby corrected as shown below:

| | |
|---|---|
| Col. 6, line 34 | Delete "contains" and insert --contain--. |
| Col. 8, line 18 | Delete "quuinazoline" and insert --quinazoline--. |
| Col. 13, line 63 | Delete "of" and insert --to-- |
| Col. 20, line 64 | Delete "17.2" and insert --17.5-- |
| Col. 24, line 61 | Delete "S(O)$_n$," and insert --S(O)$_{n'}$-- |
| Col. 26, line 15 | Delete "claim 2" and insert --claim 1 or 2--. |

Signed and Sealed this

Thirteenth Day of July 1982

[SEAL]

Attest:

GERALD J. MOSSINGHOFF

*Attesting Officer*   *Commissioner of Patents and Trademarks*